United States Patent
Bechyne et al.

(10) Patent No.: US 7,553,302 B2
(45) Date of Patent: Jun. 30, 2009

(54) PACKAGED INTERLABIAL ARTICLE

(75) Inventors: Kami Lynn Bechyne, Appleton, WI (US); Eva Rosario Sombrano Dapon, Neenah, WI (US); Thomas Patrick Keenan, Appleton, WI (US); Mary Lou McDaniel, Appleton, WI (US); Heather Ann Sorebo, Appleton, WI (US); Michelle May Sroda, Green Bay, WI (US); Susan Marie Weyenberg, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1123 days.

(21) Appl. No.: 10/744,145

(22) Filed: Dec. 22, 2003

(65) Prior Publication Data
US 2005/0137553 A1 Jun. 23, 2005

(51) Int. Cl.
*A61F 13/15* (2006.01)
*A61F 13/20* (2006.01)

(52) U.S. Cl. ............... 604/385.02; 604/385.201
(58) Field of Classification Search ............ 604/385.01, 604/385.02, 385.201, 385.17, 385.18, 904
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,041,203 A | 8/1977 | Brock et al. | |
| 4,340,563 A | 7/1982 | Appel et al. | |
| 4,766,029 A | 8/1988 | Brock et al. | |
| 5,169,706 A | 12/1992 | Collier, IV et al. | |
| 5,382,400 A | 1/1995 | Pike et al. | |
| 5,464,688 A | 11/1995 | Timmons et al. | |
| 6,010,001 A * | 1/2000 | Osborn, III | 206/440 |
| 6,131,736 A * | 10/2000 | Farris et al. | 206/440 |
| 6,183,456 B1 * | 2/2001 | Brown et al. | 604/385.01 |
| 6,203,512 B1 | 3/2001 | Farris et al. | |

(Continued)

FOREIGN PATENT DOCUMENTS

WO  WO 99/26574 A1  6/1999

(Continued)

*Primary Examiner*—Michele Kidwell
(74) *Attorney, Agent, or Firm*—Karl Sidor; Ralph Dean, Jr.; Bryan Rosiejka

(57) ABSTRACT

In one embodiment, a packaged absorbent article includes: a package and an absorbent article. The package includes a first end, a second end, and package sides extending from the first end to the second end. The first end is folded along a first fold axis toward the second end such that the package sides fold over toward an inner major surface to form a pouch with pouch sides, and the second end folded along a second fold axis toward the pouch to form a flap. The absorbent article includes a fluid permeable cover disposed over an absorbent member. The article is folded along a longitudinal axis, and the folded absorbent article is disposed in the pouch with the fluid permeable cover disposed adjacent the inner major surface. The package flap engages at least a portion of the pouch.

19 Claims, 5 Drawing Sheets

U.S. PATENT DOCUMENTS

| | | |
|---|---|---|
| 6,299,607 B1 | 10/2001 | Osborn, III et al. |
| 6,601,706 B2 | 8/2003 | McManus et al. |
| 6,705,465 B2 | 3/2004 | Ling et al. |
| 6,716,203 B2 | 4/2004 | Sorebo et al. |
| 7,178,671 B2 | 2/2007 | Nichols et al. |
| 2002/0056655 A1* | 5/2002 | Cottingham et al. ........ 206/440 |
| 2003/0023217 A1 | 1/2003 | McManus et al. |

FOREIGN PATENT DOCUMENTS

| | | |
|---|---|---|
| WO | WO 02/100311 A2 | 12/2002 |

* cited by examiner

PACKAGED INTERLABIAL ARTICLE

BACKGROUND OF THE INVENTION

This disclosure relates to a packaged feminine care articles, and especially relates to individually packaged feminine care articles.

There are two basic types of feminine protection devices: (1) sanitary napkins or pads that have been developed for external wear about the pudendal or vaginal region of a user, and (2) tampons that have been developed for residence within the vaginal cavity for interruption of menstrual flow therefrom. Each offers distinct advantages and distinct or peculiar disadvantages that may range from psychological impediments and/or concerns to physical discomfiture.

Interlabial devices, such as for use in feminine care products may be hybrid devices that combine the structural features of the sanitary napkins and tampons into a single device. Such interlabial devices fit within the vestibule of the female wearer. These interlabial devices may be characterized by having a portion that at least partially resides within the wearer's vestibule, and a portion, which at least partially resides externally of the wearer's vestibule.

Interlabial products are relatively small, enabling them to be readily concealed for discreet handling prior to use. These products do not have adhesive to adhere them to the individual package or underwear. They are worn between the vaginal lips and may be disposed of during urination leaving only the wrapper for disposal. For this reason, the benefits desired by a consumer of an individual package for an interlabial product may differ from packages used for pads and tampons. Interlabial devices need to be hygienically stored from the time they are removed from the box or bag until the article is used. This may be of particular concern with respect to maintaining a sanitary environment during placement; or if they are designed to be inserted, then during insertion and removal. There is a need for hygienically storing an individual interlabial device during transportation for maintaining hygiene, and for preventing the transfer of unsanitary particles to the pudendal or vaginal area.

Currently packaging of interlabial products does not facilitate hygienic insertion and placement. Generally, packages for tampons, sanitary pads and interlabial products are destroyed when opened. As a result, it may be difficult to insert a soiled product into the same package for disposal since part of the package is generally destroyed while opening the package. Hence, there is a need for an individual package for an interlabial device, which is durable, hygienic to handle, and preferably reusable area.

SUMMARY OF THE INVENTION

In one embodiment, a packaged absorbent article includes: a package and an absorbent article. The package includes a first end, a second end, and package sides extending from the first end to the second end. The first end is folded along a first fold axis toward the second end such that the package sides fold over toward an inner major surface to form a pouch with pouch sides, and the second end folded along a second fold axis toward the pouch to form a flap. The absorbent article includes a fluid permeable cover disposed over an absorbent member. The article is folded along a longitudinal axis, and the folded absorbent article is disposed in the pouch with the fluid permeable cover disposed adjacent the inner major surface. The package flap engages at least a portion of the pouch.

The above described and other features are exemplified by the following figures and detailed description.

DESCRIPTION OF DRAWINGS

Referring now to the figures wherein the like elements are numbered alike.

DETAILED DESCRIPTION

Disclosed herein is an individual package for an interlabial device. The package may comprise flap(s) having flap design and optional overlap, a controlled release mechanism, resealable tabs, an opening feature, perforations, pockets, and heat sealability.

The interlabial device, which may be employed for uses such as menstrual, incontinence, and/or the like, may be specifically configured to reside partially or wholly within the interlabial space of a female wearer during use. Desirably, therefore, the interlabial device is designed to have a size and geometry to fit in the pudendal region of the female anatomy, between the inside surfaces of the labia majora, including the space between the inside surfaces of the labia minora, (also known as the vestibule). Generally, therefore, the interlabial devices typically have an elongated geometry, e.g., such as in the form of an oval or the like, and a relatively small size, e.g., an overall width of about 0.5 centimeters (cm) to about 8 cm, and an overall length of about 4 cm to about 10 cm. Other suitable geometries for the absorbent article (e.g., interlabial device) include, but are not limited to, rectangular, ovoid-like, elliptical, trapezoidal, circular-like, triangular, square-shaped, teardrop like, diamond-shaped, butterfly, pear-shaped, heart-shaped, and the like, as well as a variety of combinations comprising at least one of the foregoing shapes.

Figure 1:
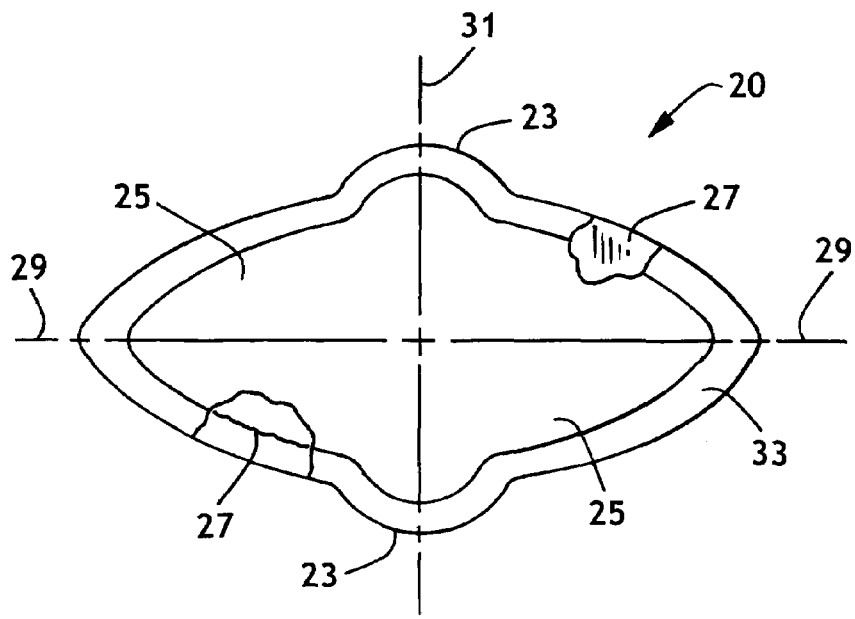
FIG. 1 is a plan view of an interlabial device such as may be packaged in accordance with this disclosure, partly broken away to show detail.
Figure 2:
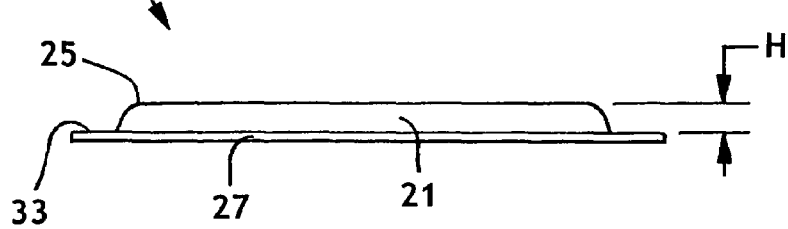
FIG. 2 is a edge view of the interlabial device.
Figure 3:
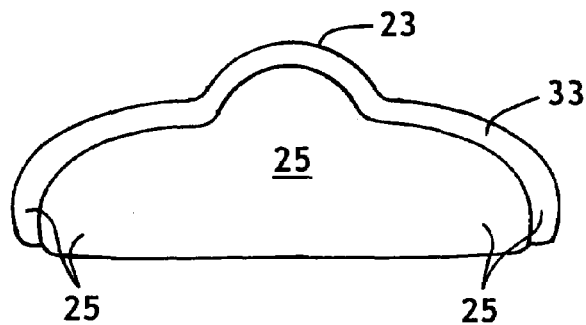
FIG. 3 is a plan view showing the interlabial device folded.

Referring now to FIGS. 1-3 that illustrate an exemplary embodiment of an absorbent article (e.g., an interlabial device) designated generally as 20. In this embodiment, the absorbent article 20 has a fluid permeable cover 25, an absorbent (or absorbent member) 21, and an optional fluid permeable baffle 27 (e.g., breathable baffle, perforated baffle, nonwoven baffle, or the like). The absorbent 21 is desirably situated between the cover 25 and the baffle 27. The absorbent article 20 is configured for disposition within the vestibule of a female wearer. The absorbent article 20 includes a principal longitudinal axis 29, a principal transverse axis 31, a body-facing surface comprising the cover 25 and a surface opposed to the body-facing surface comprising the baffle 27. The absorbent article 20 has a length, a width, a thickness, first and second spaced apart longitudinal sides, and first and second spaced apart transverse end areas. The longitudinal sides extend between the transverse end areas and collectively define the periphery of the absorbent article 20. Extending laterally outward from at least one longitudinal side of the absorbent article 20 is at least one lateral projection (e.g., tab) 23.

Describing the individual elements in greater detail, the absorbent 21 has an upper or body-facing surface and a lower surface (or surface opposed to the upper or body-facing surface) and may include any material capable of absorbing and/or adsorbing and thereafter retaining the intended bodily exudate(s). Suitable materials are also generally hydrophilic, compressible and conformable. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester and polypropylene fibers, absorbent foams, absorbent sponges, superabsorbent polymers (e.g., in the form of particles, fibers, and/or the like), coated superabsorbent polymers, fibrous bundles or nits, or any equivalent material, as well as combinations comprising at least one of the foregoing materials. Also suitable for use would be hydrophobic material that has been rendered hydrophilic. A specific example of a suitable absorbent would be similar to a coform material made of a blend of polypropylene and cellulose fibers and used in KOTEX® Lightdays pantiliners and obtainable from Kimberly-Clark Corporation, Neenah, Wis., USA.

The total absorbent capacity of the absorbent 21 should be compatible with the design exudate loading and the intended use of the absorbent article 20. Further, the size and absorbent capacity of the absorbent 21 may be varied. Therefore, the dimension, shape, and configuration of the absorbent 21 may be varied (e.g., may contain superabsorbent polymer(s), and the like). The absorbent 21 generally has a thickness, caliper or height (H), as illustrated at least in FIG. 2. The thickness of the absorbent 21 is typically less than or equal to about 10 millimeters (mm) or so, with a thickness of about 0.5 mm to about 7 mm generally employed.

Other absorbent properties include density and basis weight. The absorbent 21 desirably also has a relatively low density for enhanced comfort. Generally, the absorbent has a density of about 0.02 grams per cubic centimeter (g/cc) to about 0.5 g/cc. Meanwhile, the absorbent 21 basis weight is generally of less than or equal to about 600 grams per square meter ($g/m^2$); while typically about 0.1 $g/m^2$ to about 600 $g/m^2$, with about 200 $g/m^2$ to about 500 $g/m^2$.

The optional baffle 27 typically resides on the lower surface of the absorbent 21 and may be constructed from any desired material that is liquid-impermeable. Desirably, the baffle 27 will permit the passage of air and moisture vapor out of the absorbent 21, while blocking the passage of bodily fluid(s). An example of a suitable baffle material is a microembossed, polymeric film comprising, for example, polyethylene, polypropylene, polyester, and the like, as well as combinations comprising at least one of these polymers. This film can have a thickness of about 0.025 mm to about 0.13 mm or so. Bicomponent films, woven and nonwoven fabrics (which have been treated to render them liquid-impermeable), and/or foam (e.g., polyolefin foam and/or polyethylene foam, which may or may not be closed cell), and the like, as well as combinations comprising at least one of the foregoing, can also be used as the baffle 27. One specific example of a baffle material would be similar to a polyethylene film used on KOTEX pantiliners and obtainable from Pliant Corporation, Schaumburg, Ill., USA.

The baffle 27 may be maintained in secured relation with the absorbent 21 by bonding all or a portion of the adjacent surfaces together. A variety of bonding methods may be utilized to achieve any such secured relation. Examples of such methods include, but are not limited to, ultrasonics, thermal bonding, or the application of adhesive(s) in a variety of patterns between the two adjoining surfaces.

Disposed on a side of the absorbent 21, opposite the baffle 27, is the optional fluid permeable cover 25 having an upper surface and a lower surface, with the upper surface typically contacting the body of the wearer and receiving bodily exudate(s). The cover 25 desirably is made of a material that is flexible and non-irritating to the tissues within the vestibule of a female wearer. As used herein, the term "flexible" is intended to refer to materials which are compliant and readily conform to the bodily surface(s) or respond by easily deforming in the presence of external forces.

The cover 25 provides comfort and conformability and functions to direct bodily exudate(s) away from the body and toward the absorbent 21. The cover 25 should retain little or no liquid in its structure so that it provides a relatively comfortable and non-irritating surface next to the tissues within the vestibule of a female wearer. The cover 25 can be constructed of any woven or nonwoven material which is also easily penetrated by bodily fluids contacting its surface. Examples of suitable materials include rayon, bonded carded webs of polyester, polypropylene, polyethylene, nylon, and/or other heat-bondable fibers, polyolefins (such as copolymers of polypropylene and polyethylene), linear low-density polyethylene, aliphatic esters (such as polylactic acid), finely perforated film webs, net material, and the like, as well as combinations comprising at least one of the foregoing. A specific example of a suitable cover material would be similar to a bonded carded web made of polypropylene and polyethylene used as a cover stock for KOTEX® Lightdays pantiliners and obtainable from Sandler Corporation, Germany. Other examples of suitable materials are composite materials of a polymer and a nonwoven fabric material. The composite materials are typically in the form of integral sheets generally formed by the extrusion of a polymer onto a web of spunbond material.

A physiologically hydrous cover material is also suitable for use as the cover 25. As used herein, the term "physiologically hydrous" is intended to connote a cover material which maintains a suitably moist interface between the tissues of the vestibule and the absorbent article 20 when disposed in that vestibular environment; one that is benign respecting the requirements of comfort associated with the interposition of fabric or fabric-like structures within the moist tissue environment of the vestibule, keeping in mind as well the self-evident factor that the absorbent article is receiving bodily fluid(s) migrating through the vestibule and conducts the same to the absorbent 21. Thus, while not "hydrous" in the classic sense prior to use (inasmuch as the cover will be dry at that time) the cover maintains (or at least does not interfere with the maintenance of) the proper moisture level or balance required within the vestibule.

The cover 25 can also optionally have at least a portion of the bodyside surface treated with a surfactant to render the cover more hydrophilic. This results in permitting the insulting bodily fluid(s) to more readily penetrate the cover 25. The surfactant may also diminish the likelihood that the insulting bodily fluid(s), such as menstrual fluid, will flow off the cover rather than being absorbed by the absorbent 21. One suitable approach provides for the surfactant to be substantially evenly distributed across at least a portion of the upper surface of the cover 25 that overlays the upper surface of the absorbent 21.

The cover 25 may be maintained in secured relation with the absorbent 21 by bonding all or a portion of the adjacent surfaces together. A variety of bonding methods may be utilized to achieve any such secured relation. Examples of such methods include, but are not limited to, the application of adhesives in a variety of patterns between the two adjoining surfaces, entangling at least portions of the adjacent surface of the absorbent with portions of the adjacent surface of the cover, and/or fusing at least portions of the adjacent surface of the cover to portions of the adjacent surface of the absorbent.

The cover 25 typically resides on the upper surface of the absorbent 21, but alternatively can surround and partially, or entirely, enclose the absorbent. Alternatively, the cover 25 and the baffle 27 can have peripheries which extend outward beyond the periphery of the absorbent 21 and can be peripherally joined together to form an edge 33. With techniques, such as, for example, gluing, crimping, hot sealing, and/or the like, the edge 33 may be formed either entirely (so that the entire periphery of the absorbent 21 is circumscribed by their joinder), or partially so that the cover 25 and the baffle 27 can be partially peripherally joined. To minimize the possibility of irritation and/or discomfort to the wearer of the absorbent article 20, it is desired that the edge 33 and at least the area of the absorbent article immediately adjacent the edge be soft, compressible, and conformable.

Desirably, the edge 33 has a width of about 0.5 mm to about 10 mm, with about 0.5 mm to about 2 mm. The approximate width of any edge 33 may vary according to, inter alla, the general design and intended disposition of the absorbent article 20 within the vestibule of a female wearer. In other versions, the cover 25 and/or the baffle 27 can have a periphery that is coterminous with the periphery of the absorbent 25.

The absorbent article 20 typically is folded along the longitudinal axis 29, prior to disposition within the vestibule of the female wearer. When folded along such an axis. 29, the absorbent article 20 will form a recess which protects the wearer's finger(s) from soiling when the absorbent article is disposed within the vestibule. Once inserted, the absorbent article 20 may have a tendency to unfold in an attempt to fill the vestibule and thus maintain the upper surface (i.e., of cover 25) the absorbent article in contact with the tissues of the vestibule. The absorbent article 20 may be resiliently biased along the axis about which it is folded to increase the tendency of the absorbent article to unfold. The naturally moist surfaces of the tissues of the vestibule typically demonstrate a tendency to maintain contact with the upper surface of the absorbent article.

The wearer may hold the folded absorbent article 20 near the longitudinal sides. The absorbent article 20 may then be disposed within the vestibule by the wearer exerting a force with a finger or fingers positioned in the recess (e.g., on a side of the baffle 27 opposite the absorbent 21) formed by the folded absorbent article 20.

In order to facilitate ease of wearer handling, the absorbent article 20 may comprise at least one placement and removal tab 23 extending outward from at least one longitudinal side of an absorbent article 20. While one such tab 23 is theorized as working effectively in the placement and removal of an absorbent article 20 (e.g., a labial pad), it is believed that at least two tabs 23, i.e., one tab extending from each longitudinal side of the absorbent article, are desirable for ease of handling the article and prevention of contamination of the cover 25 by handling of the wearer. The tab(s) offer a female wearer the opportunity to grasp the tabs to aid in the disposition of a labial pad into the vestibule. In addition, the tab(s) 23 also offer a female wearer the opportunity to grasp the tabs to aid in the removal of a labial pad and thus minimize the likelihood that the female wearer's finger(s) will come into contact with the body-facing surface of the possibly soiled labial pad.

While it is not necessary, the tabs 23 are desirably identical, or, more properly, mirror images one of another. The tabs 23 may be incorporated into a number of suitably shaped and dimensioned labial pads beyond the design illustrated herein. These tab(s) 23 can be of any suitable configuration. Non-limiting examples of shapes for the tab 23 include, ovoid, elliptical, trapezoidal, rectangular, triangular, diamond-shaped, circular, semi circular, or any combination of the above. The tab 23 may be integrally formed with the absorbent article 20 or it may be a separate element joined to the absorbent article. When the tab 23 is a separate element joined to the absorbent article 20, the tab(s) 23 may be so joined by a number of methods including melt fusion, adhesion, and/or other joining means. The phrase "integrally formed" is intended to indicate that the tab(s) 23 are not joined to the absorbent article 20, but rather are an extension of: the cover 25, the baffle 27, and/or the absorbent 21 (e.g., the cover 25 and the baffle 27; the cover 25 and the absorbent 21; the baffle 27 and the absorbent 21; or the cover 25, baffle 27, and absorbent 21.

The tab 23 has sufficient dimensions to aid the female user in disposition of the absorbent article 20 within the vestibule and, optionally, removal of the absorbent article from the vestibule, wherein "sufficient dimensions" is intended to indicate that the tab 23 can be grasped between the index finger and the thumb or, if there are, for example, two tabs, between the index finger and the thumb and the middle finger and the index finger. The length of the tab(s) 23 (i.e., the longest portion of the tab(s) 23 along the dimension parallel to the longitudinal axis 29), which varies dependent upon the design and intended disposition of the absorbent article within the vestibule of a female user, is typically about 1 mm to about 100 mm, with about 5 mm to about 20 mm typical. In addition to having a length (l), the tab 23 also has a width (w). The width (w) of the tab 23 varies dependent upon the design and intended disposition of the absorbent article within the vestibule of a female user. Possible widths are about 1 mm to about 50 mm, with about 2.5 mm to about 7.5 mm generally desired.

The dimensions of the tab(s) 23 are limited only by the stress-strain properties of the tab material(s). Desirably any material used in the tab(s) 23 is soft, yet sturdy to hold with finger(s), compressible, and conformable, and thus desirably similar to the material used in the fluid permeable cover 25, the liquid impermeable baffle 27, and/or the absorbent 21. Any such material desirably minimizes the possibility of irritation and/or discomfort to the wearer.

The tab(s) 23 may be positioned in a variety of locations along the longitudinal side(s) of an absorbent article 20. With regard to the absorbent articles 20 described herein, the tab 23 may be located in the first end region, the second end region, or the central region. A second tab could at the same time be located along the opposing longitudinal sides in the first end region, the second (and opposite) end region, or the central region. Generally, when a tab 23 extend outward from a longitudinal side of a particular region, any second tab typically extends outward from the corresponding region of the opposing longitudinal side. It should also be noted that, depending on the length of the tab 23, the tab 23 may cover more than one of the regions described herein.

Some exemplary absorbent article designs as well as compositions are set forth in Patent Publications WO2002100311 A2 and WO2002100311 A2, to EDENS et al., and assigned to Kimberly-Clark Worldwide, Inc.

Figure 4:
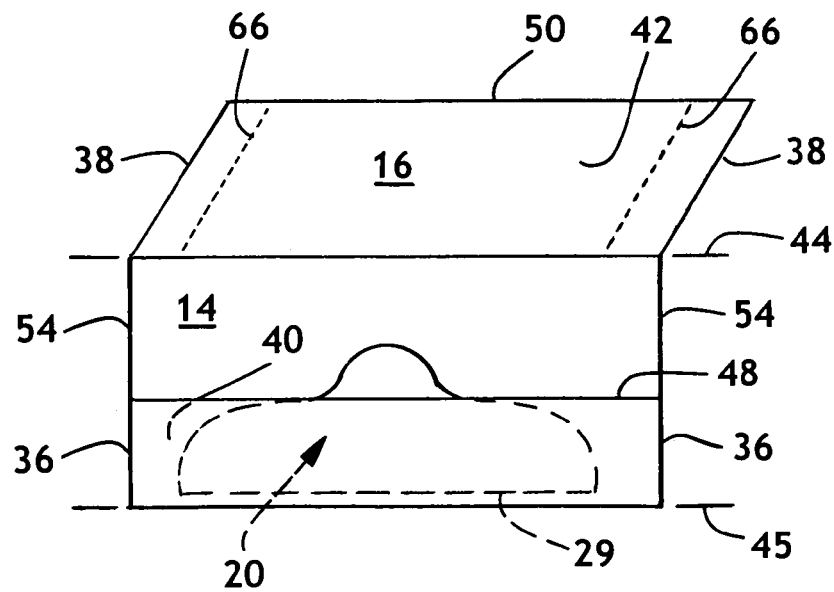
FIG. 4 is a front elevation of hygienic packaging containing the folded interlabial device.
Figure 5:
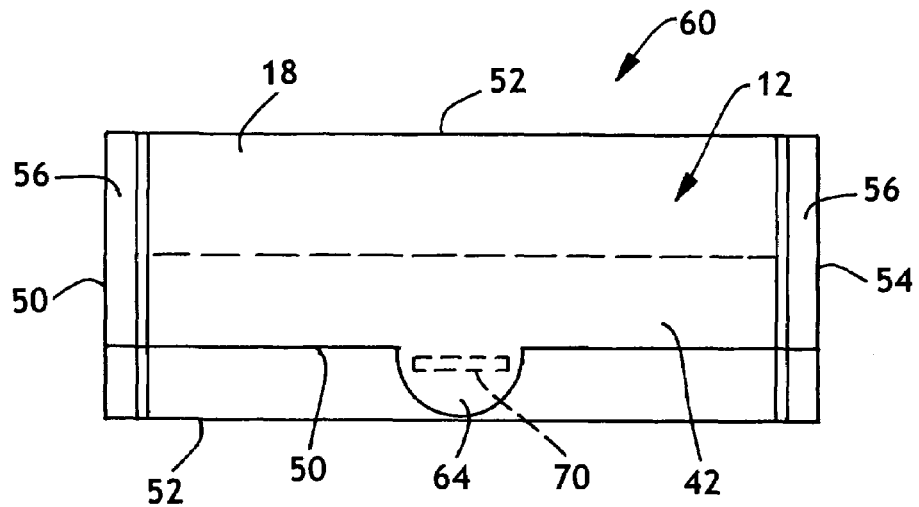

Referring to FIGS. 4 and 5, the interlabial device 20 is disposed within an individual package 60 so as to enable facile, hygienic, removal of the device 20 from the package, and optionally, reinsertion of a used device 20 into the package 60. The package 60 includes an elongated piece of wrapper material folded and bonded into a pouch configuration. For example, the wrapper material may be an elongated rectangular piece having a first end 48, an opposite second end 50, and generally parallel side edges 54 disposed therebetween.

It can be seen that the wrapper material is essentially folded around the absorbent article 20 such that the pouch 40 is formed around the article. The wrapper material may be first folded at a first fold axis 46 such that the first end 48 is folded towards but spaced from the second end 50. The distance between the first end 48 and second end 50 may vary depending on the desired length of a resulting flap 42, as described below. The generally parallel side edges 54 of the wrapper material define sides of the pouch 40. The second end 50 of the wrapper material can then be folded at a second fold axis 44 so as to extend back over the first end 48 and thus defines the flap 42 that closes off the pouch 40. The flap 42 has longitudinal sides 38 that align with the side edges 54 and pouch sides 36. The sides of the package 60 are then bonded in any manner capable of adhering the sides accordingly, for example with a heat/pressure embossing roll. Desirably, the flap 42 has longitudinal sides 38 are bonded to the side edges 54 and pouch sides 36 in a single pass operation. It may be the case that the first end 48 extends essentially to the second fold axis 44 and, thus, the longitudinal sides 38 would be bonded along their entire length to pouch sides 36.

Referring to FIGS. 5-12 it can be seen that the edge of the second end 50 extends across the front surface of the pouch 40. It may be desired to adhere all or a portion of this edge to the pouch surface, or to leave the second end 50 un-adhered to the pouch 40 between its bonded or unbonded sides. As is illustrated in the figures, various amounts of adhesion can be obtained as illustrated by the frangible seal 70. In one embodiment, the longitudinal sides 38 are not adhered to sides 36, and the flap 42 is secured to the pouch 40 with an adhesive.

The wrapper material may comprise various materials employed for sanitary, hygienic storage of feminine care products. Preferably, the interlabial device 20 and/or the package 60 are flushable and/or biodegradable, with both the interlabial device 20 and the package 60 being flushable and/or biodegradable desirable. In one embodiment, for example, a laminate material including a first film layer 16 (see FIGS. 4 and 5) laminated to a second fibrous material layer 18. The wrapper material is oriented so that the film layer 16 is disposed on the inside of the pouch 40 and thus defines an inner major surface 14.

The film layer 16 includes one or more layers of any film material that is liquid impermeable, but vapor-pervious. The film layer 16 may have any desired color and surface pattern. It may be desired that the film layer 16 have a nondescript color and pattern, such as a neutral color for product discretion. One type of film 16 that may be used is a nonporous, continuous film that, because of its molecular structure, is capable of forming a vapor-pervious barrier. Among the various possible polymeric films are films made from poly(vinyl alcohol), polyvinyl acetate, ethylene vinyl alcohol, polyurethane, ethylene methyl acrylate, ethylene methyl acrylic acid, and the like, as well as combinations comprising at least one of the foregoing materials; to make them breathable. If desired, it is also possible to add fillers to the film such as, for example, calcium carbonate and/or titanium dioxide, to increase opacity, decrease cost, and create a breathable film if the filled film is subsequently stretched. If the film layer is not sufficiently thin, then it may be necessary to further thin the film by stretching it in an apparatus such as a machine direction orienter (MDO) unit. An MDO has a plurality of stretching rollers which progressively stretch and thin the film in the machine direction (direction of travel of the film through the machine).

Another type of film that may be useful is a microporous film. These films have a number of interconnecting voids or holes that provide pathways for the transportation of water molecules from one surface to another. The passageways are sufficiently small so that only vapors and not fluids can pass therethrough.

The fibrous material layer 18 forms an outer major surface 12 of the pouch 40. As used herein, the term "fiber" or "fibrous" refers to elongated individual natural or synthetic strands (as compared to a continuous film layer), and includes discontinuous strands having a definite length and continuous strands of material, such as filaments. The fibrous layer 18 may comprise any one or combination of non-woven or woven materials, and/or bicomponent materials (e.g., fibers which may have been formed from at least two polymers extruded from separate extruders but spun together to form one fiber), and is intended to give the pouch a soft and cloth-like tactile feel and to dampen and reduce noise associated with storing, carrying, and opening the package 60. Non-woven materials may be preferred from a manufacturing standpoint. However, woven materials, including any manner of synthetic or natural cloth are contemplated herein.

As used herein the term "nonwoven" material means a web having a structure of individual fibers or threads that are interlaid, but not in an identifiable manner as in a knitted fabric. Nonwoven fabrics or webs have been formed from many processes such as, for example, meltblowing processes, spunbonding processes, bonded carded web processes, etc. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

The fibrous material layer 18 may comprise, for example, a non-woven meltblown web. Meltblown fibers are formed by extruding a molten thermoplastic material through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Generally speaking, meltblown fibers may be microfibers that may be continuous or discontinuous, are generally less than or equal to about 10 micrometers in diameter, and are generally tacky when deposited onto a collecting surface.

The fibrous material layer 18 may also or alternatively comprise a non-woven spunbond web. Spunbonded fibers are small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U. S. Pat. No. 4,340,563 to Appel, et al.; U.S. Pat. No. 3,692,618 to Dorschner, et al.; U.S. Pat. No. 3,802,817 to Matsuki et al.; U.S. Pat. No. 3,338,992 to Kinney; U.S. Pat. No. 3,341,394 to Kinney; U.S. Pat. No. 3,502,763 to Hartman; U.S. Pat. No. 3,502,538 to Levy; U.S. Pat. No. 3,542,615 to Dobo, et al.; and U.S. Pat. No. 5,382,400 to Pike, et al. Spunbond fibers are generally not tacky when they are deposited onto a collecting surface. Spunbond fibers can sometimes have diameters less than or equal to about 40 micrometers, and are often about 5 micrometers to about 20 micrometers in diameter.

The fibrous material layer 18 may comprise a spunbond/meltblown/spunbond ("SMS") material. A typical SMS material is described in U.S. Pat. No. 4,041,203 to Brock et al. Other SMS products and processes are described, for example, in U.S. Pat. No. 5,464,688 to Timmons et al.; U.S. Pat. No. 5,169,706 to Collier et al.; and U.S. Pat. No. 4,766,029 to Brock et al. Generally, an SMS material will consist of a meltblown web sandwiched between two exterior spunbond webs. Such SMS laminates have been available commercially for years from Kimberly-Clark Corporation under marks such as Spunguard® and Evolution®. The spunbonded layers on the SMS laminates provide durability and the internal meltblown layer provides porosity and additional cloth-like feel.

Suitable non-woven webs for use as the fibrous material layer 18 may also be made from bonded carded webs and airlaid webs. Bonded carded webs are made from staple fibers that are sent through a combing or carding unit that separates or breaks apart and aligns the staple fibers to form a nonwoven web. Once the web is formed, it then is bonded by various bonding method(s). Airlaying is a process by which fibrous webs can be formed. In the airlaying process, bundles of small fibers having typical lengths of about 6 millimeters (mm) to about 19 mm are separated and entrained in an airsupply and then deposited onto a forming screen, usually with the assistance of a vacuum supply. The randomly deposited fibers then can be bonded to one another using various bonding techniques.

Examples of possible materials for fibrous material layer 18 include polypropylene, polyethylene (e.g., linear low density polyethylenes), polyamides, polyesters, polycarbonates, polytetrafluoroethylenes, copolymers of ethylene (for example, ethylene vinyl acetate, ethylene-propylene rubbers), polyurethane, A-B and A-B-A' block copolymers, styrene-butadiene copolymers, propylene-butene-1 copolymers, terpolymers, and the like, as well as combinations comprising at least one of the foregoing materials.

The film layer 16 and fibrous material layer 18 are laminated together by any suitable lamination technique. Suitable lamination means include, but are not limited to, adhesives, ultrasonic bonding, and thermomechanical bonding such as through the use of heated calendering rolls. Such calendering rolls will often include a patterned roll and a smooth anvil roll, though both rolls may be patterned or smooth and one, both or none of the rolls may be heated.

It can be seen that once the absorbent article 20 is placed on the inner major surface 14 of the wrapper material, the material is folded at the first axis 46 and then at the second axis 44 to define the pouch 40 and flap 42. The sides of the pouch and flap are then bonded or sealed together. These seals or bonds can be formed by heat, heat and pressure, pressure, adhesive, ultrasonic bonding, or other types of bonding techniques. The seals can be made to be a "permanent" seal, which means that the wrapper material adjacent to the seal will tear or break before the sealed layers separate. Alternately, and desirably, the seals may be "frangible" seals, which means that the sealed layers will separate or pull apart. In a desirable embodiment of the package 60, the seal between the flap sides 38 and the pouch sides 36 is a frangible seal formed by simultaneously sealing the pouch sides and flap sides in a single sealing operation with a heated/pressure embossing roll. In another desirable embodiment of the package 60, the flap sides 38 and the pouch sides 36 are not sealed together. The flap 42 has frangible seal 70 that maintains the flap 42 disposed in contact with the pouch 40 until the consumer opens the package. Desirably, the frangible seal 70 is resealable to allow a used feminine product to be disposed in the pouch 40, the package reclosed and then discarded. Various materials maybe used as the frangible seal including adhesives can be employed, such as an adhesive tab, pressure sensitive adhesive, snap, hook and loop, and the like, as well as combinations comprising at least one of the foregoing. The preferred releasable attachment could be a hook and loop (also called touch and close) type fastening system, for instance such as sold under the trademark "VELCRO®".

Figure 8:
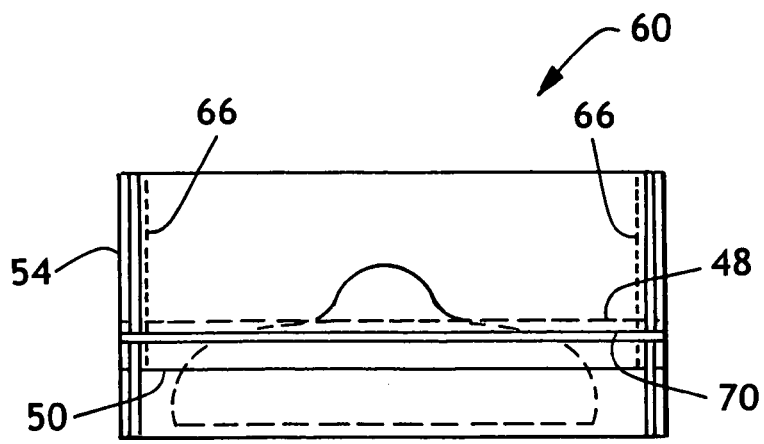
FIGS. 5-12 are side views of exemplary embodiments of individual interlabial device packages.
Figure 6:
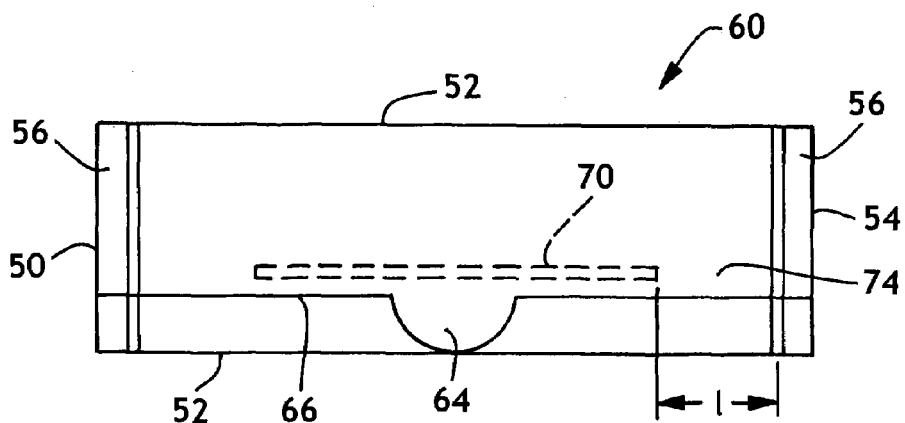
Figure 7:
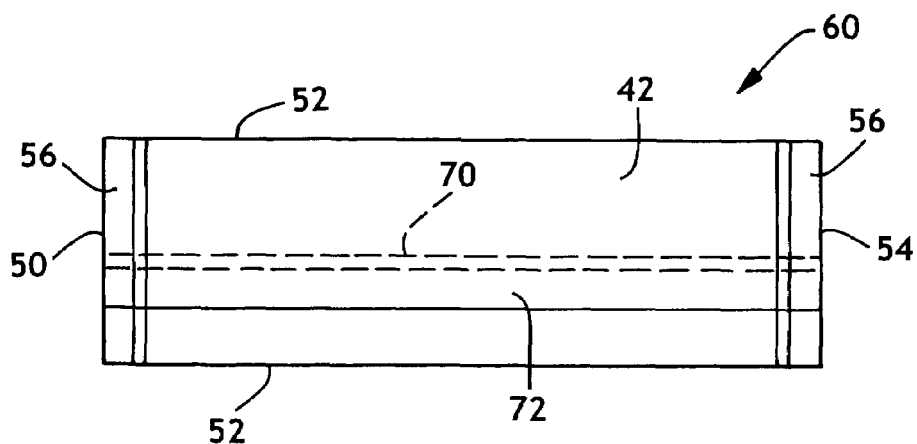
Figure 9:
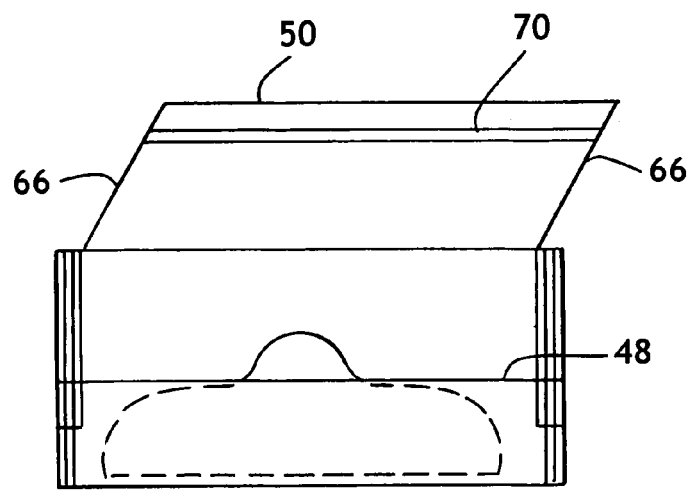

In the embodiments illustrated in FIGS. 4, 7, and 9, the consumer opens the package 60 by inserting a finger between the flap 42 and front surface of the pouch 40, and then pulling the flap 42 away from the pouch 40 or sliding the finger side-ways to break the sealed sides of the flap 42. The second end 50 is preferably not, or only partially, adhered to the front surface of the pouch and it is thus relatively easy for the consumer to insert a finger between the flap and pouch. In contrast, in embodiment illustrated in FIGS. 5, 6, and 8, the consumer opens the package 60 by pulling the package tab 64 away from the pouch 40.

Referring again to FIG. 4, where the absorbent article 20 is illustrated within an individual interlabial package 60. The absorbent article is shown folded along the longitudinal axis 29 (see FIG. 1) such that the cover 25 is on an outer surface that may contact an inner major surface 14 of package 60, and the baffle 27 is folded onto itself. When the interlabial device 20 is disposed within the pouch 40, the tabs 23 preferably protrude from the pouch 40. Therefore, the pouch 40 preferably has a sufficient size to receive the interlabial device 20 while receiving little or none of the tabs 23 (and if there are no tabs, an upper edge of the interlabial device). The interlabial device is desirably positioned within the package 60 such that the orientation of the interlabial device in the package 60 is such that the user is able to grasp an opening edge of the interlabial device 20. In an exemplary embodiment, the orientation of the interlabial device prevents foreign matter entering the package 60 from contacting the absorbent side 25 and contacts the fluid impervious layer (baffle) 27 which is folded in. Disposure of the tabs 23 (or at least edges of the interlabial device) external to the pouch 40 enables facile removal of the interlabial device from the pouch 40 when the flap 42 is opened, without contamination of the device prior to use. The particular orientation of the interlabial device 20 in the pouch enables one or more fingers, e.g., the index finger, to be inserted between the tabs 23 (e.g., in contact with the baffle 27), and the tabs 23 to then be grasped between the thumb and index finger and the index finger and middle finger (or merely between the fingers). In this orientation, the interlabial device 20 is ready to be inserted into the vestibule of the female wearer without further manipulation, folding, or the like. Therefore, the pouch 40 may partially enclose the interlabial device 20, and preferably completely enclose the interlabial device 20 except for a sufficient amount of the tabs 23 to enable facile removal from the pouch 40.

FIG. 5 is a front view of an exemplary embodiment of the individual package 60 comprising the interlabial device 20. The wrapper material forms longitudinal edges 52, side edges 54 and side panels 56. On the flap 42 is a package tab 64 to facilitate easy opening of the package 60. Beneath the package tab 64 (see FIG. 5), or along a portion (see FIGS. 6 and 13) or all (see FIGS. 7 and 8) of a side of the flap 42 that contacts the pouch (not shown in this figure), may be an adhesive. Optionally, perforations 66 may be disposed through the flap 42 and/or the pouch 40 to further enable facile opening of the package, particularly if adhesive is employed along a substantial portion of the flap 42. After its use, the interlabial device 20 may be placed back into the package 60 and resealed for disposal purposes.

FIG. 6 is a front view of an exemplary embodiment of the individual package 60. In this exemplary embodiment, there are pockets 74 at each end of the flap to allow a finger or thumb to be inserted and open the package 60. The pockets 74 have a sufficient length "l" to enable the insertion of a finger to further assist in opening of the package 60. Generally, the length l is about 5 mm to about 30 mm in length, with about 15 mm to about 25 mm in length desirable.

FIG. 7 is a front view of an exemplary embodiment of the individual package 60 without the package tab. The longitudinal edge closest to the upper portion of the interlabial device 20, and the side edges 54 are sealed to form the individual package 60. In this exemplary embodiment the flap overlaps the package and the front edge 72 of the flap enables grasping for opening and resealing purposes.

Figure 10:
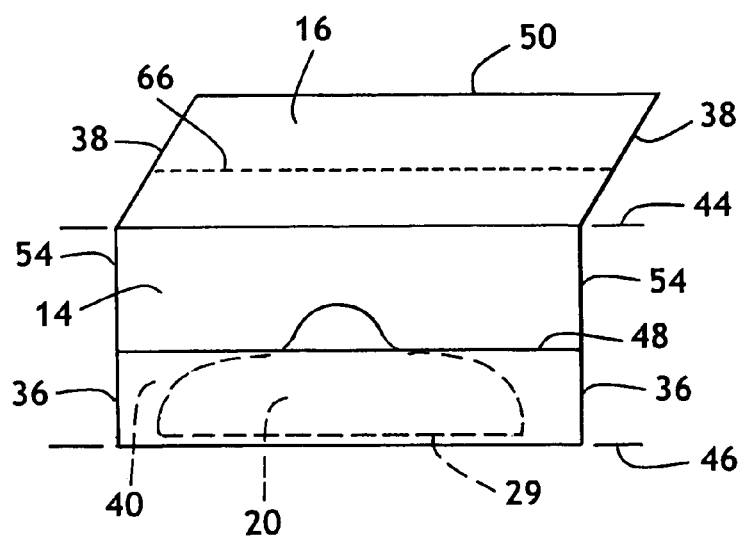
Figure 11:
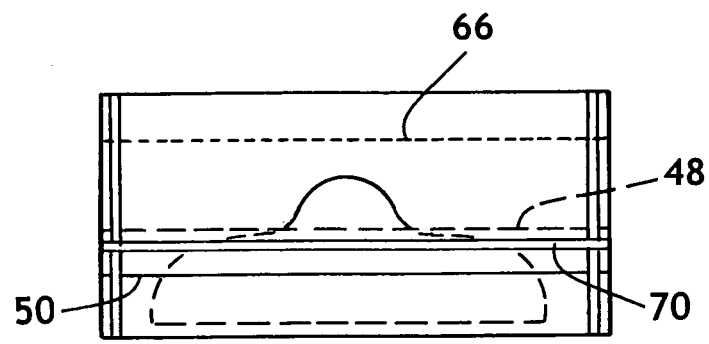
Figure 12:
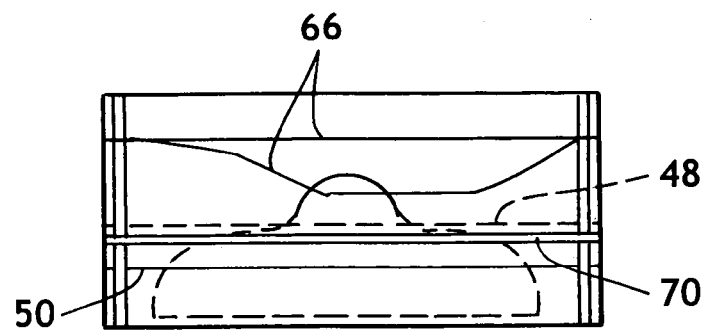

FIGS. 4, 8-12 are front views of exemplary embodiments of the individual package 60 showing perforations on flap. This embodiment, for example, would be useful with a pouch material for which the end seals do not readily peel open. The perforations 66 would allow a clean easy opening as opposed to tearing the material adjacent to the seal. FIG. 4 illustrates the location of perforations 66 in a latitudinal direction prior to folding and sealing the package. FIG. 8 illustrates the package 60 closed and sealed. FIG. 9 illustrates the pouch opened; torn at perforations 66. FIG. 10 illustrates perforations 66 in a longitudinal direction prior to folding and sealing the package. FIG. 11 illustrates the package 60 closed and sealed, while FIG. 12 illustrates the package opened; torn at perforations 66.

Another possible embodiment employs the pockets and adhesive, but does not utilize the package tab. It is noted that various variations of the present designs are possible and contemplated.

An advantage of the present disclosure is that it protects the user's fingers from touching the cover 25 of the interlabial device 20 as the device is removed from the package 60. There is also improved discretion of the individual package while carrying because of its very small size, pouch color, and minimal noise while opening. More than one package may be discreetly carried in the hand or on the body at one time. The use of subtle colors allow for blending with the carrier for visual discretion such as the colors beige, peach, white, or any other color that aids in discreet transporting. Equally important is maintaining a clean interlabial device that the user can grasp in the proper location for easy placement on the body. It is most preferred that an interlabial device is positioned within the package with the tabs exposed while opening the package to minimize the risk of the interlabial device from falling out of the package or being touched. Also, the package is durable enough so that it can be reused to wrap a soiled interlabial device prior to disposal.

While the invention has been described with reference to an exemplary embodiment, it will be understood by those skilled in the art that various changes may be made and equivalent may be substituted for elements thereof without departing from the scope of the invention. In addition, many modifications may be made to adapt a particular situation or material to the teachings of the invention without departing from the invention scope thereof. It is, therefore intended that the invention not be limited to the particular embodiment disclosed as the best mode contemplated for carrying out this invention, but that the invention will include all embodiments falling within the scope of appended claims.

What is claimed is:

1. A packaged absorbent article, comprising:
   a package comprising a first end, a second end, and package sides extending from the first end to the second end, wherein the first end is folded along a first fold axis toward the second end such that the package sides fold over toward an inner major surface to form a pouch with pouch sides, the second end folded along a second fold axis toward the pouch to form a flap;
   an absorbent article comprising a fluid permeable cover disposed over an absorbent member, wherein the article is folded along a longitudinal axis;
   wherein the folded absorbent article is disposed in the pouch with the fluid permeable cover disposed adjacent the inner major surface and the longitudinal axis of the absorbent article is parallel with first and second ends of the package;
   wherein the flap engages at least a portion of the pouch; and
   wherein the absorbent article further comprises an article tab extending from a longitudinal edge, and wherein at least a portion of the article tab protrudes from the pouch, past the first end.

2. The article of claim 1, wherein the package further comprises a film layer forming the inner major surface and adhered to a fibrous material layer forming an outer major surface of the package.

3. The article of claim 1, wherein the absorbent article further comprises a liquid impermeable-baffle, wherein the absorbent member is disposed between the fluid permeable cover and the liquid impermeable baffle.

4. The article of claim 1, wherein the flap further comprises a flap tab and wherein the package further comprises a resealable adhesive disposed on at least one of the flap and the pouch such that the flap can be adhered to the pouch.

5. The article of claim 1, wherein the package further comprises a resealable adhesive disposed on at least one of the flap and the pouch such that the flap can be adhered to the pouch, and wherein the resealable adhesive is selected from the group consisting of tapes, glues, snaps, hook and loop, thermal bonds, and a combination comprising at least one of the foregoing reseal able adhesives.

6. The article of claim 1, wherein the package further comprises a pocket disposed between the engagement of the flap and the pouch and the adjacent package side.

7. The article of claim 1, wherein the package further comprises perforations along at least a portion of the flap such that the flap can be detached from the pouch.

8. The article of claim 1, wherein the flap further comprises a tab protruding from the second end in a direction opposite the first end.

9. The article of claim 1, wherein the absorbent member further comprises a superabsorbent polymer.

10. The article of claim 1, wherein the absorbent article is an interlabial device.

11. A packaged absorbent article, comprising:
    a package comprising a first end, a second end, and package sides extending from the first end to the second end, wherein the first end is folded along a first fold axis toward the second end such that the package sides fold over toward an inner major surface to form a pouch with pouch sides, the second end folded along a second fold axis toward the pouch to form a flap;
    an absorbent article comprising a fluid permeable cover, an absorbent member, and a fluid impermeable baffle, wherein the absorbent member is disposed between the fluid permeable cover and the fluid impermeable baffle, and an article tab extending from a longitudinal edge of the absorbent article;
    wherein the folded absorbent article is disposed in the pouch with the fluid permeable cover disposed adjacent the inner major surface;
    wherein at least a portion of the article tab protrudes from the pouch past the first end; and wherein the flap removably engages at least a portion of the pouch.

12. The article of claim 11, wherein the package further comprises a film layer forming the inner major surface and adhered to a fibrous material layer forming an outer major surface of the package.

13. The article of claim 11, wherein the flap further comprises a flap tab and wherein the package further comprises a resealable adhesive disposed on at least one of the flap and the pouch such that the flap can be adhered to the pouch.

14. The article of claim 11, wherein the package further comprises a resealable adhesive disposed on at least one of the flap and the pouch such that the flap can be adhered to the pouch, and wherein the resealable adhesive is selected from the group consisting of tapes, glues, snaps, hook and loop, thermal bonds, and a combination comprising at least one of the foregoing resealable adhesives.

15. The article of claim 11, wherein the package further comprises a pocket disposed between the engagement of the flap and the pouch and the adjacent package side.

16. The article of claim 11, wherein the package further comprises perforations along at least a portion of the flap such that the flap can be detached from the pouch.

17. The article of claim 11, wherein the flap further comprises a tab protruding from the second end in a direction opposite the first end.

18. The article of claim 11, wherein the absorbent article is folded along a longitudinal axis and the longitudinal axis of the absorbent article is parallel with first and second ends of the package.

19. The article of claim 11, wherein the absorbent article is an interlabial device.

* * * * *